United States Patent [19]

Krispel

[11] Patent Number: 5,006,759
[45] Date of Patent: Apr. 9, 1991

[54] TWO PIECE APPARATUS FOR ACCELERATING AND TRANSPORTING A CHARGED PARTICLE BEAM

[75] Inventor: Franz Krispel, Walnut Creek, Calif.

[73] Assignee: Siemens Medical Laboratories, Inc., Walnut Creek, Calif.

[21] Appl. No.: 191,633

[22] Filed: May 9, 1988

[51] Int. Cl.$^5$ .................. H05H 7/08; H05H 7/10
[52] U.S. Cl. .................. 315/5.41; 313/359.1; 313/361.1; 328/228; 328/233; 250/396 R; 250/398
[58] Field of Search ............... 315/5.41, 5.42, 5.35, 315/5.34, 5.29, 5.24, 5.26; 313/359.1, 360.1, 361.1; 328/227, 228, 233, 234; 250/396 R, 396 ML, 398

[56] References Cited

U.S. PATENT DOCUMENTS

| | | | |
|---|---|---|---|
| 3,379,911 | 4/1968 | Enge | 250/398 |
| 3,778,655 | 12/1973 | Luce | 313/363.1 |
| 3,867,635 | 2/1975 | Brown et al. | 250/396 R |
| 4,198,565 | 4/1980 | Ono | 250/398 X |
| 4,293,772 | 10/1981 | Stieber | 250/492.2 |
| 4,455,489 | 6/1984 | Brown | 250/398 |
| 4,719,436 | 1/1988 | Garwin et al. | 333/252 |
| 4,804,879 | 2/1989 | Fukumoto | 313/361.1 |

FOREIGN PATENT DOCUMENTS

| | | |
|---|---|---|
| 561135 | 3/1958 | Belgium . |
| 0060771 | 7/1975 | European Pat. Off. . |
| 0173926 | 9/1984 | European Pat. Off. . |
| 6714692 | 10/1967 | Netherlands . |
| 2054542 | 7/1980 | United Kingdom . |

OTHER PUBLICATIONS

Froelich, H. R., "Design of a Shuttle Microtron for Radiation Therapy"; *IEEE Transaction on Nuclear Science*; vol. NS-24, No. 3, Jun. 1977; pp. 1022–1024.

Uhlmann et al., "The Linear Electron Accelerator as Source of Fast Electrons for Cancer Therapy", Jun. 1956, pp. 859–870.

C. J. Karzmark, "Advances in Linear Accelerator Design for Radiotherapy", 1984, Med. Physics, p. 105 to 128.

*Primary Examiner*—Eugene R. LaRoche
*Assistant Examiner*—Benny Lee
*Attorney, Agent, or Firm*—Lawrence C. Edelman

[57] ABSTRACT

Apparatus for accelerating and transporting a charged particle beam. The apparatus has a housing which encases an accelerating structure as well as a magnet system. The accelerating structure accelerates an injected charged particle beam within a first evacuated space and directs the beam into the magnet system which transports it along a bent beam path within a second evacuated space. Both spaces are separate from each other and the magnet system is supported within the housing such that it can be angularly adjusted with respect to the accelerating structure. In a preferred embodiment, the second evacuated spaced is partially defined by magnet poles of the magnet system and filled with helium under a pressure of higher than $10^{-2}$ torr.

12 Claims, 3 Drawing Sheets

TWO PIECE APPARATUS FOR ACCELERATING AND TRANSPORTING A CHARGED PARTICLE BEAM

BACKGROUND OF THE INVENTION

The invention relates to an apparatus for accelerating and transporting a beam of charged particles. In particular, it relates to an electron linear accelerator (LINAC) used in radiotherapy.

A typical LINAC contains a vertical stand and a gantry supported by the stand so that it can rotate around a horizontal axis ("isocenter"). The gantry has two horizontally extended arms one of which houses an electron source, an accelerating structure and, at its outer end, a beam bending magnet system and a so called "lower treatment head" encasing various elements for transforming the bent beam into the final treatment beam. The treatment beam is then projected through the isocenter to a beam detector mounted at the outer end of the other arm which also carries a counter weight for balancing the gantry bearing.

The bending system, which typically consists of a vacuum-tight beam envelope surrounded by a number of magnet poles, coils and flux return elements, should be designed so that it not only translates incoming particles with different energies and trajectories into a tight parallel beam, but also affords a low isocenter and reduced torques at the gantry bearing.

To obtain good electro-optical qualities, magnet systems have been developed which deflect the electron beam by 270°. These systems, examples of which are described in Medical Physics 11 (1984) pages 105 to 128, in particular section V, D., have reasonably low isocenters but are relatively heavy and bulky. Moreover, they are mechanically complicated because special steps must be taken to maintain an extremely high vacuum of about $10^{-9}$ torr in the envelope and to avoid thermal stresses in the exit window (see, for instance U.S. Pat. No. 4,293,772).

It is therefore an object of this invention to provide a charged particle beam accelerating and transporting apparatus having acceptable beam transportation characteristics and being nonetheless small and light.

It is another object of this invention to provide a charged particle beam accelerating and transporting apparatus which makes it possible for a LINAC to have a lower isocenter.

It is a further object of this invention to provide a charged particle beam accelerating and transporting apparatus which is of a simple construction and, in particular, does not require special means to prevent the beam windows from being overheated.

It is yet another object of this invention to improve on existing apparatus for accelerating and transporting a charged particle beam.

SUMMARY OF THE INVENTION

The invention is directed to an apparatus for accelerating and transporting a beam of charged particles having high energies, i.e. energies in the MeV range. This apparatus has a housing supporting an accelerating structure and a magnet system for bending the beam. The accelerating structure has a first envelope which encloses a first evacuated space. This structure accelerates the charged particles within the first evacuated space and emits them along a first beam axis. The magnet system has a second envelope which encloses a second evacuated space. This system transports the emitted beam within the second evacuated space along a bent path and emits it along a second beam axis. Both evacuated spaces are separate from each other. The accelerating structure and the magnet system are mounted such that the second envelope can be angled with respect to the first beam axis.

The invention procedes from the following observation: In conventional arrangements, the envelopes of both the accelerator and the bending magnet form a single vacuum system. They are therefore rigidly connected with each other in a vacuum-tight fashion. In practice, such a connection, normally a welded joint, cannot be constructed precisely enough to insure that the envelope within the magnet is always exactly aligned with the first beam axis. Consequently, this envelope is relatively wide and there is an additional margin provided between opposite magnet poles so that the bending system can be accurately oriented with respect to the injected beam, no matter whether its envelope is misaligned and/or warped. As a result, the whole assembly is oversized and heavy, for it takes strong magnets to build up the required magnetic fields. However, in accordance with the present invention, the beam bending system is mechanically decoupled from the accelerating structure and the magnet system may first be preassembled (and internally aligned) and subsequently aligned with respect to both beam axes. This way, the gap between opposite magnet poles may be kept small, inasmuch as now these poles may themselves form the side walls of the magnet envelope. As a consequence, all parts including the yoke can be smaller and lighter so that the overall volume (including the extension along the second beam axis), weight and power consumption of the magnet system are significantly reduced.

The invention is relatively simple, in that the window mountings need not be vacuum-tight, and none of the windows must be placed at a site where the beam has a very small diameter, i.e. where the window would be subject to local overheating.

The beam steering qualities of the invention are good even though the beam passes through relatively long non-evacuated sections before it enters the lower beam treatment head. This is because the magnet system guides and confines all charged particles which enter the system within a certain angular departure and lateral displacement from the beam axis and within a certain energy range around a central value. Even if the beam is widened on its way between the accelerating structure and the magnets, the bending system can be made to receive virtually all charged particles; and once the particles have entered the system they are properly focussed even if the beam must leave the evacuated space somewhat earlier than it exits the magnet system.

An apparatus in accordance with the present invention has another, and unexpected, advantage: its elimination of welds helps to extend the service life of the electron source. In conventional systems, the accelerator and the magnet envelope are, as mentioned above, welded together. This weld joint contains trapped carbon atoms, which are gradually released by the RF fields of the accelerator and by straying beam electrons. The liberated carbon atoms are easily ionized and contribute to a dark current that eventually contaminates the electron cathode. In an apparatus according to the invention, however, the accelerating structure can be sealed without welds, using techniques and materials which do not cause the beam source to deteriorate.

In a preferred embodiment of the invention, the beam bending system deflects the beam by 270°, and the first evacuated space is sealed by a beam exit window and the second evacuated space is sealed by a beam entrance window as well as a beam exit window. Furthermore, the diverted beam crosses the first beam axis between the beam exit window of the first evacuated space and the beam entrance window of the second evacuated space.

In another preferred embodiment of the invention, the beam exit window of the magnet system is designed and placed so that it not only seals the evacuated space but also serves as an energy selection filter. Such a filter, which is described for example in the above cited article, Section V.F, is formed by two vanes which are located at a site where the radial displacement of a particle trajectory from the center orbit corresponds to the deviation of the momentum of the particle from a given value. The vanes project into the beam and by intercepting outer beam parts they only let through particles with energies within a certain range centered around a nominal value. At the filter side, the beam is especially wide so that the window is not likely to be thermally overstressed.

In still another embodiment of the invention, the second evacuated space is filled with a gas whose effective cross-section for the charged particles is smaller than that of air. Such a gas filling allows for a relatively soft vacuum without impairing the overall electro-optical qualities of the system. If electrons are to be transported, the filling is preferably helium, particularly $He^3$ under a pressure of higher than $10^{-2}$ torr.

According to a specific aspect of the invention, the beam is diverted by 270° in the magnet system which in turn is supported so that the treatment beam may pivot around the first beam axis in a plane perpendicular to this axis. Such a beam movement is desirable for certain treatments, for instance if the patient's thorax wall is to be irradiated.

The foregoing and other objects, features and advantages of the invention will be apparent from the following more particular description of preferred embodiments of the invention, as illustrated in the accompanying drawings.

DETAILED DESCRIPTION OF THE PREFERRED EMBODIMENTS

Figure 1:
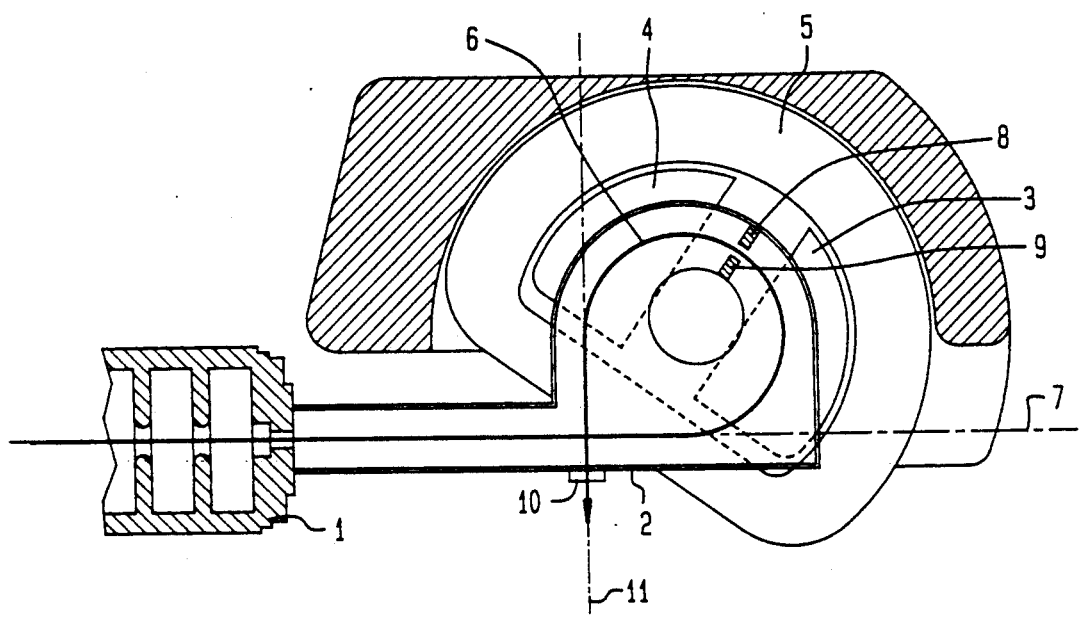
FIG. 1 illustrates an accelerating structure magnet system from a conventional LINAC, as viewed in cross-section along the beam bending plane, with some parts taken or broken away.

FIG. 1 shows, from a known LINAC, the end section of an accelerating waveguide structure 1, an envelope 2 and a magnet system comprising magnet poles 3, 4, a coil unit 5 and a yoke for returning the magnetic flux. In operation, a pulsed electron beam 6 is injected into the waveguide structure 1 by a cathode (not shown), then accelerated (to about 10 MeV) and finally emitted along a horizontally extended first beam axis 7 into envelope 2. Within the magnet system the electrons are subject to magnetic fields which bend the electron trajectories through 270°. On its way through the magnet system, the beam passes an energy selection filter with two vanes 8, 9 and leaves the envelope 2 through window 10 along a second beam axis 11, travelling towards the isocenter.

Envelope 2 is welded to the waveguide structure 1 so that both the accelerating section of the waveguide and the interior of envelope 2 form one common vacuum system. The air pressure in this system is on the order of $10^{-9}$ torr, because the accelerating section requires a high vacuum. To accomodate misalignments, envelope 2 has a width of about 9 millimeters across the bending plane, and corresponding magnet poles are about 20 millimeters apart.

Figure 2:
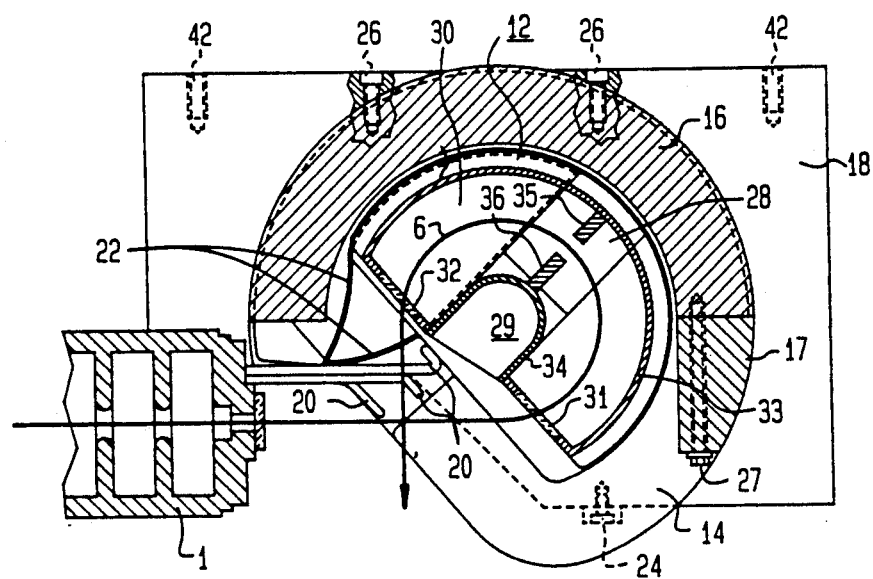
FIG. 2 shows a first preferred embodiment of the invention, as viewed in cross-section along the bending plane.
Figure 3:
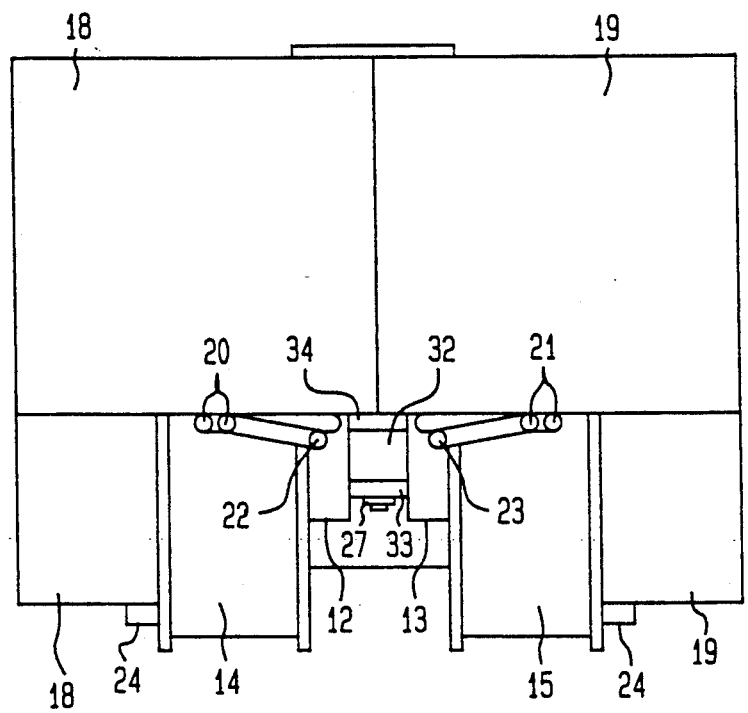
FIG. 3 is a side view of the magnet system of the first preferred embodiment, as viewed along the first beam axis.
Figure 4:
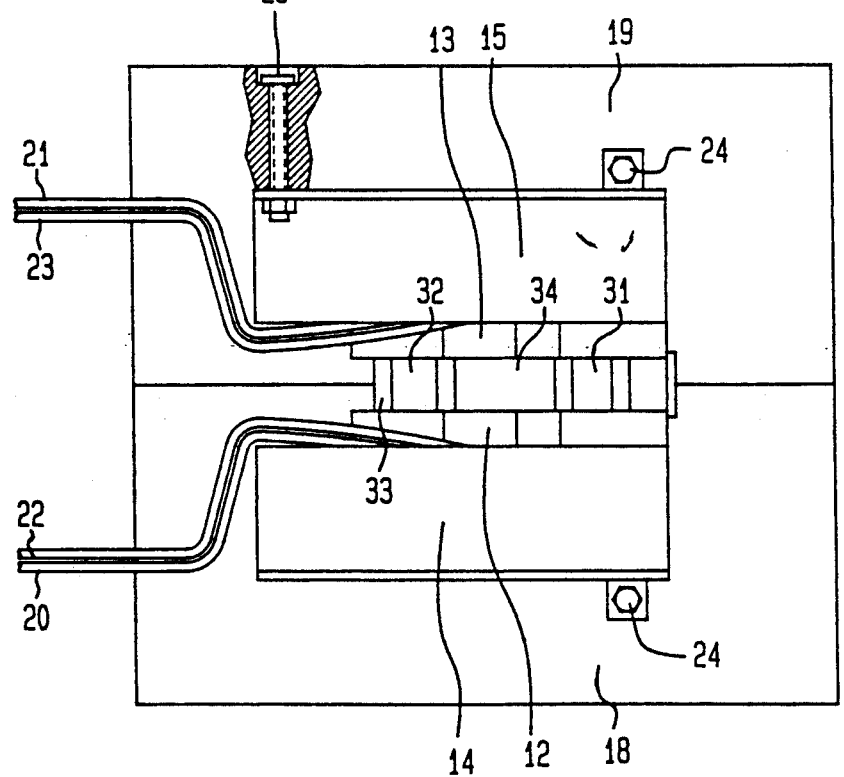
FIG. 4 is a bottom view of the magnet system of the first preferred embodiment.

Since FIG. 2 is a cross sectional view and FIGS. 3 and 4 are a side view and bottom view, respectively, not all reference numbers are shown in all of these Figs. Reference numbers 13, 15, 19, 21 and 23 are shown only in FIGS. 3 and 4 and reference number 25 is shown only in FIG. 4. FIGS. 2 to 4 illustrate a first embodiment of the invention. Here again, an electron beam 6 is accelerated in a waveguide structure 1 and bent by 270° in a magnet system. The system has two magnet poles 12, 13, two coil units 14, 15 which are spaced by a metal rim composed of two parts 16, 17, and a yoke providing the magnetic return path. This yoke is composed of two halves 18, 19 bolted together.

To remove heat from the coils, their windings are exposed to a cooling liquid transported through pipes 20, 21. Each coil is connected to a current source (not shown) via wires 22, 23, and attached to the yoke via screws 24, 25. The yoke not only holds the coils but also keeps in place, via screws 26, the metal rim whose parts 16, 17 are in turn connected to each other by means of a bolt 27.

Each magnet pole 12, 13 has a cross-section which (see FIG. 2) resembles the letter D. Where the magnet poles 12, 13 face each other, they have parallel surfaces which are parallel to the bending plane (here, the plane of the paper in FIG. 2) except in regions 28 and 29. At region 28 each magnet pole 12, 13 is tilted, and at region 29, each magnet pole 12, 13 is recessed, to modify the magnetic field there.

Between the magnet poles 12 or 13, there is provided a vacuum tight envelope 30 bonded by an entrance window 31, an exit window 32, an outer rim 33, an inner rim 34, and both magnet poles 12, 13. This envelope contains an energy selection slit with two vane 35, 36 and is filled with helium (particularly $He^3$) under a pressure of $10^{-2}$ torr.

Each window 31, 32 is advantageously an aluminum-coated BeO disk, which is transparent for high energy electrons and extremely temperature resistant.

Figure 5:
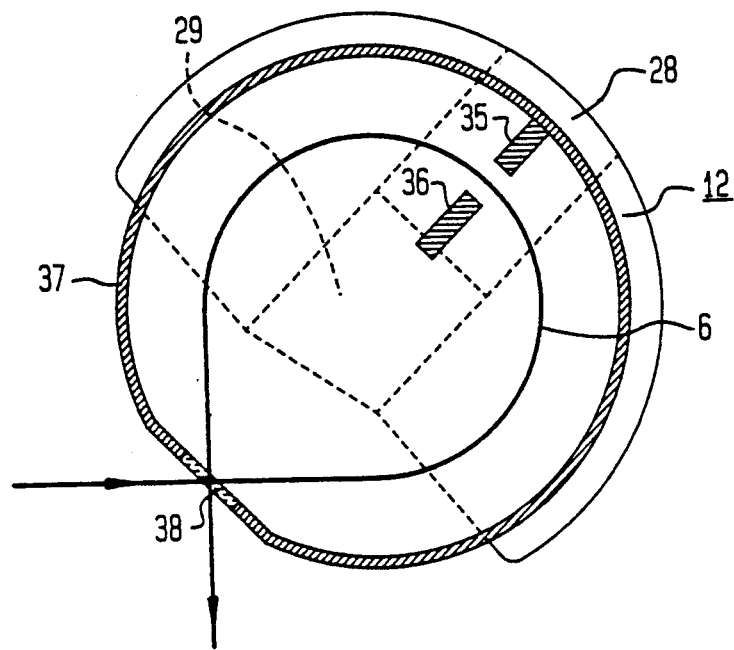
FIG. 5 illustrates one of the magnet poles and the envelope from the magnet system of a second preferred embodiment, as viewed in cross-section along the bending plane.

To reduce the number of windows and thereby simplify the construction, the shape of the envelope may be modified such that the same window serves to receive and emit the electron beam 6. Such a construction is illustrated in FIG. 5 showing one magnet pole 12 and an envelope whose walls are defined by the magnet poles, a metallic piece 37 and a window 38.

Figure 6:
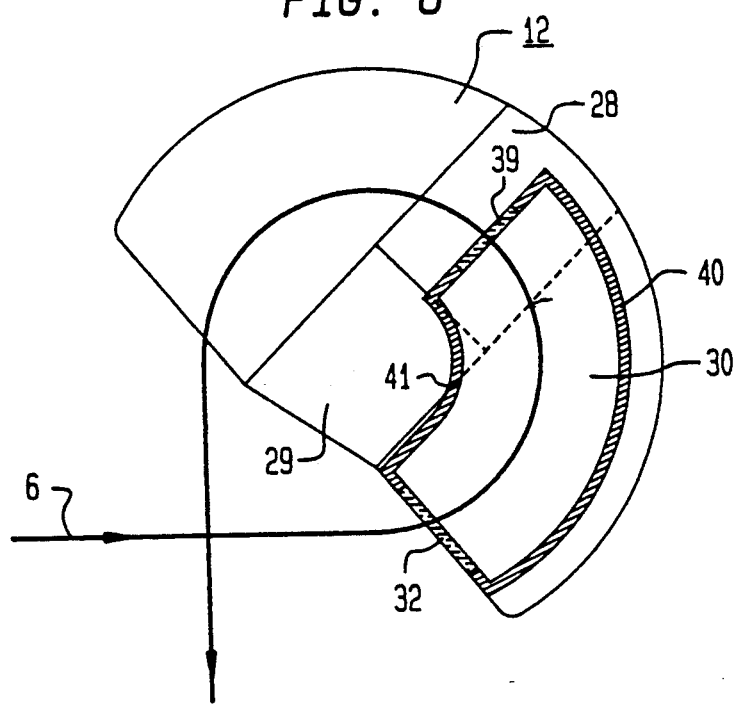
FIG. 6 illustrates one of the magnet poles as well as the envelope from the magnet system of a third preferred embodiment, as viewed in cross-section parallel to the bending plane.

In still another embodiment (FIG. 6), the envelope has two windows 32, 39 connected to each other by two rims 40, 41. In this embodiment, the envelope is shorter for the exit window 39 serves as an energy selection filter and is placed at the symmetry plane of the magnet system in which the beam is bent by 135°.

In all embodiments, the waveguide structure 1 and the yoke of the magnet system are mounted on a support (not shown), the yoke being fixed by three adjustment screws (not shown) which are threaded into tapped bores are indicated by reference numerals 42 in FIG. 2. By means of these screws the yoke can be moved with respect to the waveguide structure 1. As a result, the envelope 30, the field configuration and the bending plane can be aligned with respect to the beam axis 7. To make the beam axis 11 oscillate around the beam axis 7, the support need only be suspended so that it can pivot around the beam axis 7.

Having thus described the invention with particular reference to preferred forms thereof, it will be obvious to those skilled in the art to which the invention pertains, after understanding the invention, that various changes and modifications may be made therein without departing from the spirit and scope of the invention as defined by the claims appended hereto.

I claim:

1. Apparatus for accelerating and transporting a charged particle beam, comprising:
   (a) an accelerating structure having a first envelope which encloses a first evacuated space, said accelerating structure accelerating the charged particle beam within the first evacuated space and emitting the accelerated charged particle beam from said first evacuated space along a first beam axis;
   (b) a magnet system having a second envelope which encloses a second evacuated space, said second evacuated space being evacuated substantially less than said first evacuated space so that the pressures in said first and said second evacuated spaces are in a ratio of at least $10^4$ to 1, said second envelope receiving the charged particle beam emitted along said first beam axis by the accelerating structure, and transporting the charged particle beam within the second evacuated space along a bent beam path and emitting the charged particle beam from said second evacuated space along a second beam axis having a spatial orientation which is different from the first beam axis; and
   (c) supporting means for supporting the accelerating structure and the magnet system such that the position of the second envelope with respect to the first beam axis is physically movable so as to adjust the spatial orientation of said first beam axis with respect to said second beam axis.

2. Apparatus according to claim 1, wherein the first envelope is sealed by a first window through which the charged particle beam is emitted, and wherein the second envelope is sealed by a second window through which the charged particle beam enters the second evacuated space.

3. Apparatus according to claim 2, wherein the second envelope is further sealed by a third window through which the charged particle beam leaves the second evacuated space.

4. Apparatus according to claim 3, wherein the charged particle beam has a circular cross-section with a given beam diameter upon entering the second envelope and is transported by the magnet system such that said charged particle beam changes its diameter along the bent beam path, and wherein the third window is placed at a site where the beam diameter is largest.

5. Apparatus according to claim 2, wherein the charged particle beam is bent within the magnet system by 270° and intersects the first beam axis between the first and second windows.

6. Apparatus according to claim 1, wherein the magnet system comprises two magnet poles on opposite sides of the bent beam path, said magnet poles forming sidewalls of the second envelope.

7. Apparatus according to claim 1, wherein the magnet system is pivotally supported within a housing so that the second beam axis is movable relative to the first beam axis in a plane perpendicular to the first beam axis.

8. Apparatus for accelerating and transporting a charged particle beam, comprising:
   (a) an accelerating structure having a first envelope which encloses a first evacuated space, said accelerating structure accelerating the charged particle beam within the first evacuated space and emitting the accelerated charged particle beam from said first evacuated space along a first beam axis;
   (b) a magnet system having a second envelope which encloses a second evacuated space, said second envelope receiving the charged particle beam emitted along said first beam axis by said accelerating structure, and said magnet system transporting the charged particle beam within the second evacuated space along a bent beam path and emitting the charged particle beam from said second evacuated space along a second beam axis having a spatial orientation which is different from the first beam axis; and
   (c) supporting means for supporting the accelerating structure and the magnet system such that the position of the second envelope with respect to the first beam axis is physically movable so as to adjust the spatial orientation of said first beam axis with respect to said second beam axis, and
   wherein said first envelope is sealed by a first window through which the charged particle beam is emitted, and the second envelope is sealed by a second window through which the charged particle beam enters the second evacuated space and a third window through which the charged particle beam leaves the second evacuated space, and
   wherein the charged particle beam is transported by the magnet system such that at one site along the bent beam path the charged particles are radially displaced from a central orbit according to the difference between their momentum and a nominal momentum, and wherein the third window is placed at said one site and is designed such that it intercepts the charged particles with momentum outside a predetermined momentum range containing the nominal momentum.

9. Apparatus according to claim 8, wherein the charged particle beam is bent by 270° and the third window is placed at a site where the charged particle beam is bent by 135°.

10. Apparatus for accelerating and transporting a charged particle beam, comprising:
(a) an accelerating structure having a first envelope which encloses a first evacuated space, said accelerating structure accelerating the charged particle beam within the first evacuated space and emitting the accelerated charged particle beam from said first evacuated space along a first beam axis;
(b) a magnet system having a second envelope which encloses a second evacuated space, said second envelope receiving the charged particle beam emitted along said first beam axis by said accelerating structure, and said magnet system transporting the charged particle beam within the second evacuated space along a bent beam path and emitting the charged particle beam from said second evacuated space along a second beam axis having a spatial orientation which is different from the first beam axis; and
(c) supporting means for supporting the accelerating structure and the magnet system such that the position of the second envelope with respect to the first beam axis is physically movable so as to adjust the spatial orientation of said first beam axis with respect to said second beam axis, and
wherein the second evacuated space contains a gas whose effective cross section for the charged particles is lower than that of air.

11. Apparatus according to claim 10, wherein the charged particles are electrons, the gas is helium and the helium pressure is higher than $10^{-2}$ torr.

12. Apparatus according to claim 11, wherein the gas is $He^3$.